United States Patent [19]

Sogi et al.

[11] 4,179,339
[45] Dec. 18, 1979

[54] LIQUID FEEDER FOR AUTOMATIC CULTURE APPARATUS

[75] Inventors: Shinroku Sogi; Makoto Yoshinaga, both of Hachioji; Toshio Shinohara, Chofu; Takayuki Aihara; Ikuo Tawara, both of Hachioji, all of Japan

[73] Assignee: Olympus Optical Company, Ltd., Tokyo, Japan

[21] Appl. No.: 876,894

[22] Filed: Feb. 13, 1978

[30] Foreign Application Priority Data

Mar. 2, 1977 [JP] Japan .............................. 52-24766[U]
Apr. 5, 1977 [JP] Japan .............................. 52-41589[U]
Apr. 5, 1977 [JP] Japan .............................. 52-41592[U]

[51] Int. Cl.² .............................................. C12K 1/10
[52] U.S. Cl. .................................. 435/292; 285/192; 435/287
[58] Field of Search ...................... 195/127, 139, 142; 285/138, 192

[56] References Cited

U.S. PATENT DOCUMENTS

| | | | |
|---|---|---|---|
| 3,574,064 | 4/1971 | Bennings et al. ..................... | 195/127 |
| 3,672,953 | 6/1972 | Coty et al. ......................... | 195/139 X |
| 3,772,154 | 11/1973 | Isenberg et al. ................. | 195/127 X |
| 3,799,844 | 3/1974 | Campbell et al. .................... | 195/127 |
| 3,957,585 | 5/1976 | Mabik .............................. | 195/142 X |

Primary Examiner—Alvin F. Tanenholtz
Assistant Examiner—Robert J. Warden
Attorney, Agent, or Firm—Ostrolenk, Faber, Gerb & Soffen

[57] ABSTRACT

A liquid feeder comprises a liquid suction and delivery pump which withdraws a liquid such as a culture solution, buffer solution, enzyme solution or the like which is retained in a liquid storage container as refrigerated or at a reduced temperature and delivers it through a flexible tube for injection into a culture vessel located within an incubator. The tube is inserted into an inner pipe and is sealingly secured thereto. The inner pipe is detachably and hermetically mounted in an outer pipe which extends through and is secured to a wall forming an environment isolating layer of the incubator. An eccentric crankpin which is driven by a motor is connected through a link with another crankpin having a greater eccentricity, the latter crankpin being driven for rotation to cause a reciprocatory rotating motion of a driven shaft about its own axis through an angular extent of less than 180°. The motion of the driven shaft is effective to selectively switch the discharge port of a pair of liquid supply tubes to a position over a single vessel. The motor also drives a cam which causes a vertical motion of a drive shaft which is also angularly driven by a cam groove, the drive shaft being effective to cause a three dimensional motion of the discharge port of a single liquid supply tube for injection into a pair of vessels.

8 Claims, 13 Drawing Figures

LIQUID FEEDER FOR AUTOMATIC CULTURE APPARATUS

BACKGROUND OF THE INVENTION

The present invention relates to a liquid feeder for automatic culture apparatus, and more particularly to a liquid feeder for injection of a liquid such as a culture, buffer or enzyme solution into a culture vessel in an automatic culture apparatus in which biological tissues or cells are automatically cultured.

The technique of culturing biological tissues and cells represents an essential fundamental experimental process in various fields including the medical, biological, pharmaceutical and agricultural fields. However, the culture of biological tissues and cells over successive generations involve a technical difficulty, which prevents a stable strain being cultured from being obtained in practice. Thus, there has been a need for a procedure for culturing biological tissues and cells which enable a stabilized strain being cultured to be obtained. Recently, a culture technique in a gaseous environment within an incubator has been developed, and has enabled the culturing over successive generations of cells of a particular variety such as those of liver, neuron, pituitary gland which have been considered difficult to be cultured.

The culture over successive generations will be briefly summarized below. A given number of cells is diluted in a culture solution in the form of a suspension, which is injected into a culture vessel such as petri dish. The vessel is placed in an incubator which cultures the cells under a given gas atmosphere. After a predetermined period of time, the vessel is removed from the incubator and the number of growth of cells are counted under a microscope. When it is determined that the intended cells have grown over the full extent of the vessel, it is transferred to a strain-free clean bench and the culture solution in the vessel is withdrawn with a pipette and disposed. Subsequently, a buffer solution is injected into the vessel to clean the remaining cells, and then withdrawn for disposal with a pipette. The grown cells which attach to the bottom of the vessel are rendered freely removable therefrom by the injection of an enzyme solution such as trypsin and allowing the vessel to remain intact for a given period. After the predetermined period, the enzyme solution is withdrawn from the vessel with a pipette and disposed, and a culture solution is again injected into the vessel. The culture solution is repeatedly withdrawn and discharged through the pipette to cause an oscillation or agitation which enables the grown cells to be completely released from the bottom of the vessel and suspended in the culture solution. The cells in suspension are transferred into a centrifuge tube with a pipette, and placed in a centrifuge to separate the cells from the solution. Thereupon the cells attach to the bottom of the tube while the culture solution will be a decantered solution, which is disposed by tilting the tube. A culture solution is again injected into the centrifuge tube and is agitated by utilizing the withdrawing and discharging operation through the pipette to separate the cells from each other so that they are uniformly suspended in the culture solution within the centrifuge tube. Finally, the solution is distributed into a pair of culture vessels in an equal amount to complete one culture operation.

It will be recognized by those skilled in the art that the foregoing culture technique make it necessary to remove the culture vessel out of the incubator and to expose it to the outer atmosphere in order to examine the growth of the tissues or cells under a microscope. This causes a sudden change in the culture conditions since the cells or tissues are placed out of a given environment maintained within the incubator including a gas atmosphere, temperature and humidity. This causes a delicate influence upon the tissues or cells being cultured and also involves an unavoidable contamination thereof by miscellaneous strains present in the atmosphere.

In addition, the various operations required for culturing over successive generations which should take place based on the results of observation with the microscope rely on a manual operation by an operator in the clean bench. This means that any slight difference in the various operations from operator to operator may have a direct influence upon the culturing result of the tissues or cells. Since the experience and skill of culturing technique varies from operator to operator, it is difficult to provide a standard procedure for the culturing technique, and this makes it impossible to obtain cultured tissues or cells of uniform quality. As a consequence, for different groups of researchers conducting a common study on the same theme, the conclusions reached may depend on the quality of the tissues being cultured. In extreme cases, the conclusions may be opposite to each other. Thus it will be seen that the reliability cannot be expected when the tissues or cells are cultured with the conventional technique.

It is generally accepted that it takes at least two years to train a skilled operator. As a result, there exists, a continued demand for skilled operators. As a consequence, researchers often have to perform the culturing operation themselves rather than devotedly directing their efforts to their study.

In view of these considerations, the present invention is directed to an automatic culture apparatus capable of automatically performing the above described culturing operation. As a result, the present invention eliminates the contamination which may occur as a result of the exposure to the atmosphere, eliminates the influence of manual operations upon the cultured results and permits a standard and uniform procedure for the various culturing operations to be established.

An automatic culture apparatus meeting the above requirements must be provided with a liquid supply system or liquid feeder which supplies various liquids or solutions such as buffer, enzyme and culture solutions to the culture vessel or centrifuge tube. The liquid supply system must include a refrigerator for storing the buffer, enzyme or culture solution. This refrigerator cannot, however, be housed within an incubator having a limited capacity since a large quantity of such solutions is required. As a result, it is necessary to provide a liquid supply from outside the incubator to a given location within the incubator maintained under a predetermined environment. In addition, the entire liquid feeder must be sterilized before it is assembled with the automatic culture apparatus. If the feeder is disassembled before sterilization the parts may be subjected to contamination by strains during the assembly which follows the sterilization step, adversely influencing the subsequent culturing operation. It is desireable, therefore, to design the entire feeder so that is can be sterilized without requiring the disassembly thereof. It is also desirable that the liquid feeder be designed such that it can be mounted to extend into the incubator so that it is easily detachable in order to permit its replacement by a fresh feeder whenever the stored solution or solutions are exhausted. In addition, a leakage of the atmosphere through the connection must be prevented.

After a buffer solution is injected into the vessel of the automatic culture apparatus, it becomes necessary to switch the supply from a buffer solution to an enzyme solution since it is desired to inject the enzyme solution into the same vessel. The conventional practice is to inject two different solutions selectively into the same vessel. This has been done utilizing a pair of separate injection pumps which are connected with supply tube of the respective solutions. The tubes have their discharge port located above the vessel, and the pumps are separately operated. However, the location of the discharge port of the respective supply tubes above the vessel was undesirable since residual solution sometimes dripped down from the port after the injection of the solution ceased resulting in a possible contamination of the vessel. Accordingly, the prior art technique was inadequate for a culturing procedure for which a high accuracy is required.

During the culturing operation, it is also required for the liquid feeder to provide a three dimensional movement of a single discharge port in order to inject the culture solution into a culture vessel and a centrifuge tube which are located at different sites. The conventional practice has been to use a pair of motors, one for vertical movement and the other for rotation. In order to control the termination or stop position of the vertical and rotational movements, there must be provided four limit switches in total, which resulted in a complex arrangement, which is also liable to malfunctioning by the failure of the limit switches.

SUMMARY OF THE INVENTION

It is a first object of the invention to provide a liquid feeder for automatic culture apparatus which may be used to inject a variety of liquids such as a culture, buffer and enzyme solution stored under refrigeration in storage containers into a culture vessel located within an incubator by means of a liquid suction and delivery pump and a liquid supply tube wherein the tube is inserted into an inner one of a pair of inner and outer pipes mounted in a wall of the incubator, constituting an environment isolating layer, the tube being sealed and secured to the inner pipe, thus facilitating the replacement of a liquid feeder.

It is a second object of the invention to provide a dual liquid supply switching system for automatic culture apparatus in which two different liquids can be selectively injected into a common vessel and wherein individual supply tubes have their discharge port arranged for movement out of the region of the vessel whenever the injection does not take place, using a simple arrangement.

It is a third object of the invention to provide a liquid feeder for automatic culture apparatus which supplies a single liquid to a pair of vessels which assume different three dimensional positions, by utilizing a simple arrangement, incorporating a pair of limit switches and a single motor to achieve a three dimensional movement of a liquid discharge port.

With the liquid feeder of the invention, the exhausted liquid feeder can be replaced by a fresh one, unscrewing the inner pipe from the outer pipe and withdrawing the inner pipe therefrom. The sterilization of the liquid feeder can be accomplished while it is in assembled form, thus reducing the influence of contaminations which might occur when the feeder is disassembled for purpose of sterilization. With the dual liquid switching system of the invention, the discharge port associated with each liquid is located above the common vessel only when that liquid is to be injected, and is moved out of the position over the vessel whenever the injection is completed, thus avoiding an adverse influence upon the culturing operation as may be caused by the undesirable dripping of the liquid.

The three dimensional switching system of the invention achieves a three dimensional movement of the discharge port with a single motor and a pair of microswitches rather than a pair of motors and four limit switches as has been conventional, thus simplifying the arrangement. The failure is also reduced, assuring a reliable operation of the system.

DESCRIPTION OF PREFERRED EMBODIMENT

Figure 1:
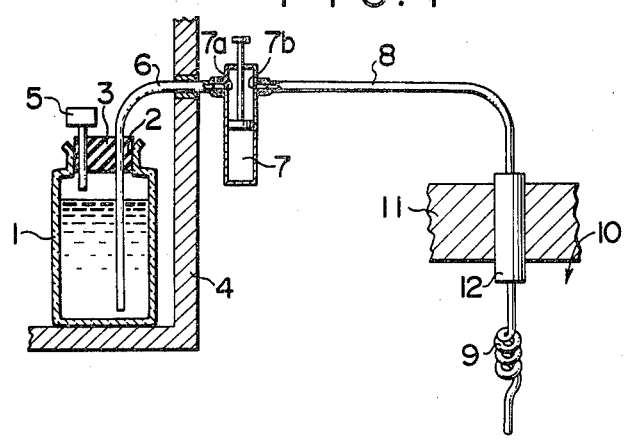
FIG. 1 is a schematic side elevation of the liquid feeder for automatic culture apparatus according to one embodiment of the invention.

Referring to FIG. 1, there is shown a storage container 1 for storing a culture, a buffer or an enzyme solution. The container 1 has a top opening 2 which is usually closed by a plug 3 formed of silicone resin. The container is normally stored in a refrigerator 4. The plug 3 is provided with a pre-filter 5 which allows communication with the atmosphere while maintaining the inside of the container 1 strain-free. One end of a first tube 6 extends through and is fixedly mounted in the plug 3 for connecting the container 1 with a liquid suction and delivery pump 7, the open free end of the tube being immersed into the liquid. The other end of the tube 6 is connected with a suction port 7a of the pump 7, which also has a delivery port 7b connected with one end of a second liquid supply tube 8, formed by a flexible tube. The other end of the tube 8 is formed with a helical winding 9 and is directed to a given site such as a culture vessel or centrifuge tube which is located within an incubator maintained under a specified environment 10. It will be seen that the free end of the second tube 8 extends through an inner pipe of a fitting 12 and has its free end disposed within the incubator. The fitting 12 comprises a pair of inner and outer pipes and is mounted in a wall 11 which represents the environment isolating layer of the incubator.

Figure 2:
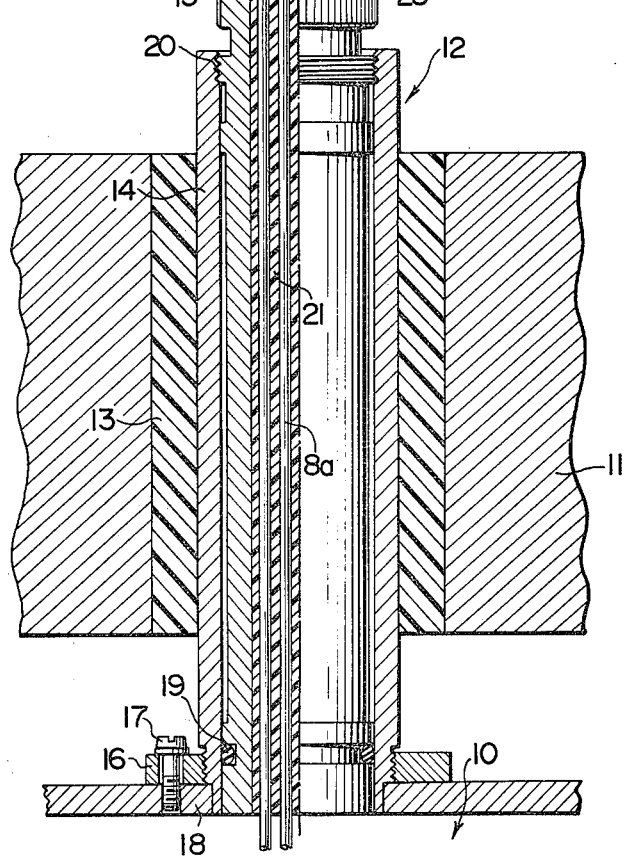
FIG. 2 is an enlarged longitudinal section, of a tube fitting.

The detailed construction of the fitting 12 is shown in FIG. 2. Fitting 12 comprises an outer pipe 14 extending through the wall 11 and sealingly secured to the wall 11 by a silicone filler 13, and an inner pipe 15 which is hermetically and detachably disposed within the outer pipe 14. The lower end of the outer pipe 14 opens into the environment 10 of the incubator, and is peripherally provided with an integral mount 16, which is firmly secured to the ceiling plate 18 of the incubator by set screws 17. An O-ring 19 is disposed between the pipes 14, 15 to prevent the leakage of the environment from the incubator to the exterior through the clearance between them. On the outer periphery of its top, the inner pipe 15 is formed with a threaded portion 20 for clamping threadable engagement with the outer pipe 14. The free end of the second tube 8 is passed through the inner pipe 15, and the portion 8a thereof which is located within the pipe is hermetically secured to the pipe 15 by silicone filler 21 which fills the space therein. Where the fitting 12 is also used with another liquid feeder of a similar construction but which is used to supply a different liquid, a second tube 22 of said another liquid feeder can be secured within the inner pipe 15 together with the tube 8 by means of silicone filler 21.

In operation, the container 1 is placed within the refrigerator 4, and the fitting 12 is used to pass the second tube 8 through the wall 8 of the incubator, with the free end of the tube 8 being directed toward a given site therein, namely, toward a culture vessel or centrifuge tube. When the pump 7 is set in operation, the liquid from the container 1 is fed through the tubes 6, 8 into the interior of the incubator from the outside thereof, and while it passes through the helical winding formed in the tube 8, it is heated to the temperature maintained within the environment 10 before it is supplied to the culture vessel or centrifuge from the inner end of the tube 8.

When the liquid in the container 1 is exhausted, an operator may hold and turn a knurled end 23 formed at the top of the inner pipe 15 to unscrew it, thus withdrawing the inner pipe 15 from the outer pipe 14. In this manner, the entire liquid feeder can be removed from the incubator, and can be replaced by a fresh liquid feeder which is filled with a full quantity of liquid. The fresh liquid feeder is sterilized while it is entirely in assembled condition, and the inner pipe 15 connected with the second tube 8 may be inserted into the outer pipe 14 and threadably engaged therewith by utilizing the threaded portion 20. Then the free end of the tube 8 will be directed toward a culture vessel or centrifuge tube located within the incubator, and the liquid feeder is ready for operation when the container 1 is received within the refrigerator 4.

When mounting the liquid feeder, the leakage of the environment 10 is positively prevented by the silicone fillers 13, 21 and O-ring 17, assuring a liquid supply without causing a contamination of the incubator.

Figure 3:
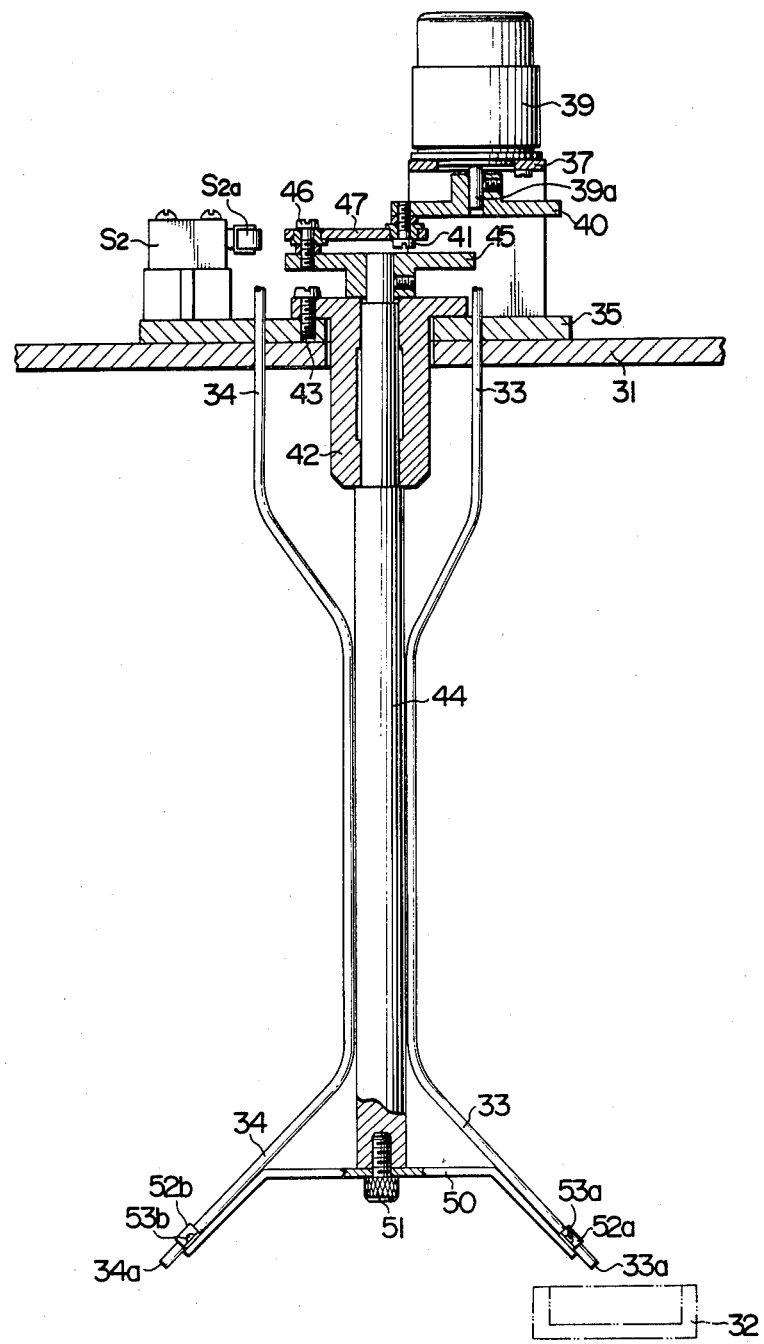
FIG. 3 is a side elevation, partly in section, of a dual liquid supply switching system according to another embodiment of the invention.

FIG. 3 shows a dual liquid supply switching system. An outer plate or wall of the incubator of the automatic culture apparatus is shown at 31 while a culture vessel 32 is shown at the bottom of this Figure. A flexible tube 33 is provided for supplying a buffer solution and another flexible tube 34 is provided for supplying an enzyme solution. A framing plate 35 is secured to the wall 31 by means of screws 36 (see FIG. 6) and a motor mounting rack 37 is fixedly mounted on the plate 35 by means of screws 38 (see FIG. 6). A motor 39 is mounted on the rack 37 and has its output shaft 39a directed downward. A drive rotating plate 40 is fixedly mounted on the output shaft 39a, on which a first crankpin 41 is fixedly mounted at a given eccentricity $l_1$ (see FIG. 6) from the shaft 39a.

Figure 4:
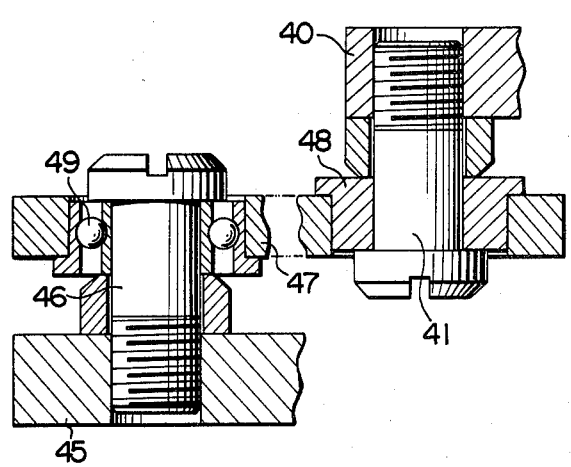
FIG. 4 is an enlarged cross section, of crankpins shown in FIG. 3.

A sleeve bearing 42 with a flange extends through the plate 35 and the wall 31 and is secured to the plate 35 by means of screws 43. The sleeve rotatably receives a driven shaft 44 of a suitable length which extends into the incubator. A driven rotating plate 45 is fixedly mounted on the end of the shaft 44 which projects outside the incubator, and a second crankpin 46 having a greater eccentricity $l_2$ than the eccentricity $l_1$ (see FIG. 6) is fixedly mounted on the rotating plate 45. The both crankpins 41, 46 are connected together by a link 47 of a given length so that the driven shaft 44 undergoes a reciprocatory angular motion about its own axis through an arcuate angular extent which is less than 180° as the motor 39 rotates. Referring to FIG. 4, it will be seen that the first crankpin 41 is rotatably mounted on the link 47 by means of a bearing 48 while the second crankpin 46 is rotatably mounted on the link 47 by means of a ball bearing 49.

Figure 5:
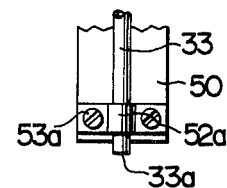
FIG. 5 is a fragmentary side elevation, showing the detail of a mounting structure provided at the free end of the tube shown in FIG. 3.

Returning to FIG. 3, the lower end of the driven shaft 44 fixedly carries a tube support plate 50 extending to the opposite sides thereof, the plate being secured to the shaft by a screw 51. The free end of the supply tube 33 is secured to one end of the tube support plate 50 by using a fixture 52a (see FIG. 5) and screw 53a while the free end of the supply tube 34 is secured to the other end of the tube support plate 50 by using a fixture 52b and screw 53b.

Figure 6:
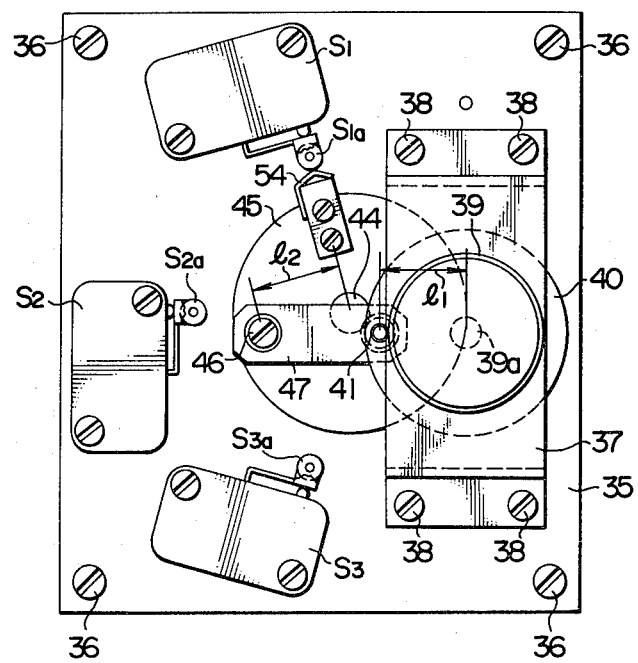
FIG. 6 is a plan view of the arrangement shown in FIG. 3.

As shown in FIG. 6, the driven plate 45 fixedly carries a switch operating member 54 which is adapted to engage an actuator S1a of a stop microswitch S1, which is operated when the driven plate 45 has rotated to the vicinity of one of the limits of its angular movement. The switch S1 is mounted on the framing plate 35. Also mounted on the plate 35 are a momentary stop microswitch S2 and another stop microswitch S3, both of which are adapted to be operated by the operating member 54 at an intermediate position and at the other limit of the angular movement of the driven plate 45, respectively. When the operating member 54 engages one of the microswitches S1 to S3, the angular movement of the driven shaft 44 is momentarily stopped.

Figure 9:
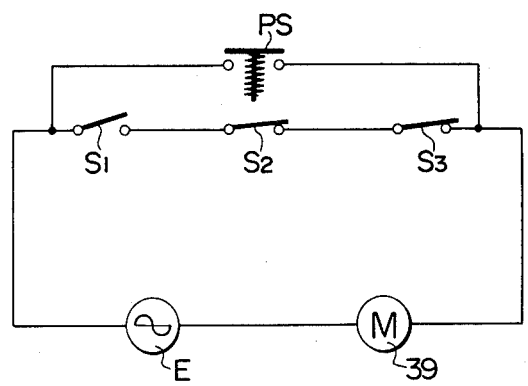
FIG. 9 is a wiring diagram of one exemplary electrical circuit which may be used in the dual liquid switching system shown in FIG. 3.

FIG. 9 shows one exemplary circuit arrangement of the dual liquid switching system. The microswitches S1 to S3 are connected in series with the drive motor 39 across a power source E, and the series combination of the microswitches S1 to S3 is shunted by a pushbutton switch PS. The switches S1 to S3 are normally closed microswitches, and are opened when they are engaged by the operating member 54. It should be understood that the circuit arrangement may be modified to provide an automatic operation in response to a signal from a timer.

When it is unnecessary to know the particular location at which the respective discharge ports 33a, 34a of the individual tubes 33, 34 stop, the mounting position of the operating member 54 and the microswitches may be reversed. With this arrangement, the provision of a single switch will be sufficient.

Figure 7:
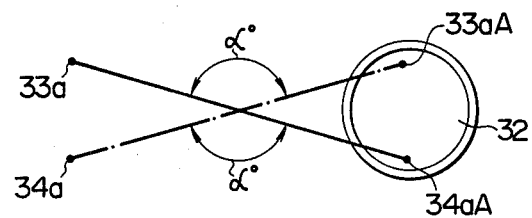
FIG. 7 is a diagrammatical view illustrating the movement of the individual discharge ports relative to a culture vessel.

The operation of the apparatus will now be described. In FIGS. 3, 6 and 7, the discharge port 33a of the tube 33 is at injection position 33aA, and since the switch operating member 54 is engaged with the actuator S1 of the microswitch S1 to open it, the motor 39 remains at rest. Under this condition, the buffer solution is injected into the vessel through the tube 33. Upon completion of the injection, when the switch PS is once depressed to be closed, the motor 39 rotates in a counter-clockwise direction as viewed in FIG. 6, with consequence that the driven rotating plate 45 also rotates in the same direction to move the operating member 54 away from the actuator S1a to close the switch S1. Thus, the motor 39 continues to rotate if the switch PS is released and allowed to open. The motor 39 is stopped when the operating member 54 engages the actuator S2a to open the switch S2. Since this stop position represents an intermediate position, the both discharge ports 33a, 34a are moved out of the region above the vessel 32. Hence, any dripping of the liquid from the individual tubes 33, 34 cannot cause an adverse influence upon the culturing operation since such liquid cannot enter the vessel 32.

When the switch PS is depressed again, the motor 39 is set in motion to cause the driven rotating plate 45 to rotate further in the counter-clockwise direction. As before, the motor 39 continues to rotate when the switch PS is opened since the operating member 54 moves away from the actuator S2a to close the microswitch S2.

The motor 39 stops at a position where the operating member 54 engages the actuator S3a of the microswitch S3. The discharge port 34a of the tube 34 which supplies the enzyme solution has moved to injection position 34aA above the vessel 32, as shown in FIG. 7, so that the enzyme solution can be injected into the vessel. When the motor 39 is set in motion again upon completion of the injection of the solution, the driven plate 45 now rotates clockwise, as viewed in FIGS. 6 and 8, since it is located at its other limit position of its angular movement, and when it reaches the intermediate position, the motor is stopped by the action of the microswitch S2. Consequently, any liquid dripping from the discharge ports 33a, 34a cannot find its way into the vessel 32.

When the motor 39 is set in motion subsequently, the driven plate 45 continues to rotate clockwise, and the motor is stopped at the limit position where the operating member 54 engages the actuator S1a of the microswitch S1. At this position, the discharge port 33a of the tube 33 is located at injection position 33aA (see FIG. 7) above the vessel 32, and hence the buffer solution can be injected into the vessel.

Figure 8:
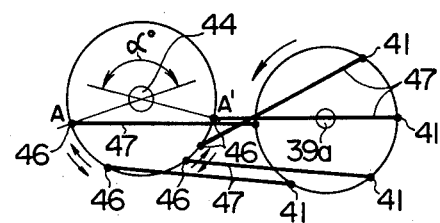
FIG. 8 is a diagrammatical view illustrating the relationship between a drive and a driven rotating plate.

In this manner, the rotation of the motor 39 causes a reciprocatory motion of the second crankpin 46 on the driven plate 45 along a segment of a circle $\overline{AA'}$ as shown in FIG. 8. It results from the fact that the eccentricity $l_2$ of the second crankpin 46 is greater than the eccentricity $l_1$ of the first crankpin 41. Denoting the angle subtended by the segment $\overline{AA'}$ by $\alpha°$, the following inequalities and equality apply:

$$l_1 < l_2, \alpha° < 180°$$

$$l_1 = \overline{AA'}/2 = l_2 \sin(\alpha/2)$$

As will be noted from FIG. 7, the discharge ports 33a, 34a of the tubes 33, 34 rotate through $\alpha°$ to place the discharge ports 33a, 34a above the vessel 32 in alternate fashion.

From the foregoing decription, it will be understood that since the eccentricity $l_1$ is less than the eccentricity $l_2$ in the present apparatus, the angular extent through which the driven shaft 44 rotates is less than 180°, thus preventing any overrunning rotation in the event the limit switches, shown above in the form of microswitches, fail. As a result, the flexible tubes 33, 34 extending along the shaft 44 cannot be twisted along the shaft 44 to cause a damage to the apparatus in the event of occurrence of an excessive rotation.

Figure 10:
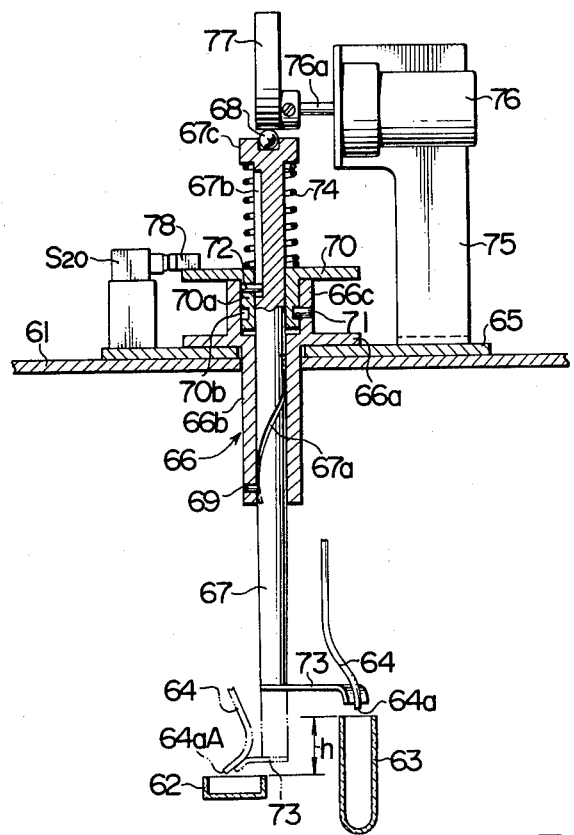
FIG. 10 is a side elevation, partly in section, of a three dimensional liquid supply switching system according to a further embodiment of the invention.

FIG. 10 shows a three dimensional supply switching system. There is shown a stationary outer plate 61 of an incubator of the automatic culture apparatus while a culture vessel located at a given position within the incubator is shown at 62. A centrifuge tube 63 is located at a position which is higher by "h" in elevation than the vessel 62 and in a vertical plane which is by $\alpha°$ (see FIG. 12) rotated from the latter. A flexible tube 64 may be used to supply a culture solution to the vessel 62 and the tube 63, respectively.

The switching system according to the invention includes a baseplate 65 which is secured to the outer plate 61 of the incubator at a given position. A hollow shaft 66 has a flange 66a, a lower cylindrical portion 66b of a reduced diameter extending downwardly from the flange 66a, and an upper hollow shaft portion 66c of a greater diameter extending upwardly from the flange 66a. The hollow shaft 66 is secured to the baseplate 65 by means of its flange 66a so that the lower cylindrical portion 66b extends through the baseplate 65 and the outer plate 61. A drive shaft 67 is inserted into the lower shaft portion 66b for vertical movement and rotation therein. Intermediate its length, the shaft 67 is peripherally formed with a helical cam groove 67a, and its top portion is formed with a keyway 67b. The shaft 67 has a bulging head 67c having an upper end face which is formed to receive a steel ball 68 in a freely rotatable manner. The lower cylindrical portion 66b fixedly carries a pin 69 which engages the cam groove 67a.

A disc-shaped rotating plate 70 includes a short sleeve 70a which is rotatably received between the upper shaft portion 66c and the drive shaft 67. Around its outer periphery, the sleeve 70a is formed with a peripheral groove 70b which is engaged by a pin 71 fixedly carried by the shaft portion 66c. The upper shaft portion 66c fixedly carries a key 72 which engages the keyway 67b, whereby the rotating plate 70 is adapted to rotate integrally with the drive shaft 67, but is prevented from its vertical movement.

A tube support arm 73 extends laterally from the bottom end of the drive shaft 67, and a flexible tube 64 which supplies a culture solution and which is introduced into the incubator from the outside thereof has its free end secured to the free end of the arm 73. A coiled compression spring 74 is disposed between the rotating plate 70 and the head 67c to urge the drive shaft 67 upwardly. A bracket 75 is fixedly mounted on the baseplate 65 and carries a drive motor 76 having an output shaft 76a on which is fixedly mounted an eccentric cam 77, the cam serving to raise and lower the drive shaft 67 through the steel ball 68.

A switch operating member 78 is fixedly mounted on the rotating plate 70. A microswitch or limit switch S10 is fixedly mounted on the baseplate 65 so as to be operated by the member 78 when the discharge port 64a of the tube 64 is located above the vessel 62. Similarly, another microswitch or limit switch S20 is fixedly mounted on the baseplate 65 so as to be operated by the member 78 when the discharge port 64a is located above the centrifuge tube 63, thus forming an angular position detecting mechanism (see FIG. 12).

Figure 13:
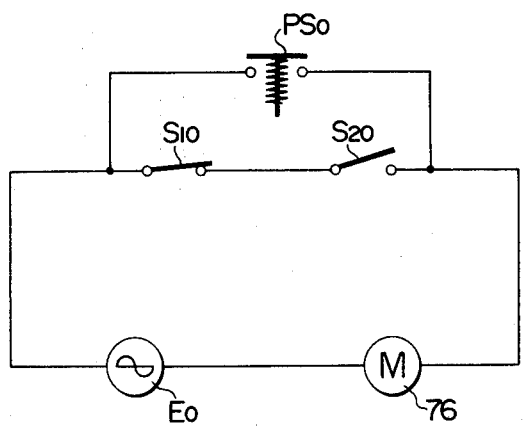
FIG. 13 is a wiring diagram of one exemplary electrical circuit which may be used in the three dimensional switching system shown in FIG. 11.

FIG. 13 shows one exemplary electrical circuit which may be used in the three dimensional switching system mentioned above. The both limit switches S10, S20 which are used to stop the motor form a series circuit together with the drive motor 76 across a power source $E_O$. The series combination of the both limit switches is shunted by a pushbutton switch $PS_O$ which is provided for switching the drive. The switches S10 and S20 are normally closed microswitches and are opened when they are operated by the member 78. It should be understood that the circuit arrangement shown may be modified to enable an automation so that the pushbutton switch $PS_O$ is depressed in connection with the operation of other apparatus or devices contained in the automatic culture apparatus. Alternatively, it may be operated with a timer.

Figure 12:
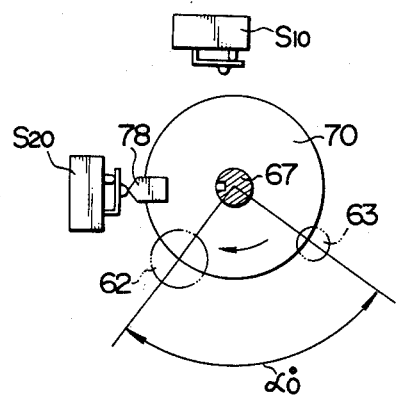
FIG. 12 is a plan view of a rotating plate and an angular position detecting mechanism.

In the condition shown in FIG. 10, the tube 64 which supplies the culture solution has its discharge port 64a located above the centrifuge tube 63, and the operating member 78 is now in engagement with the limit switch S20 to open the circuit (see FIGS. 12 and 13). As a consequence, the motor 76 remains at rest, and the culture solution can be injected into the centrifuge tube 63 during such interval.

Figure 11:
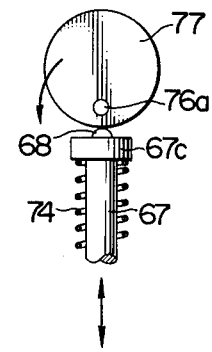
FIG. 11 is a front view of a cam which is used to move a drive shaft up and down.

When the pushbutton switch $PS_O$ is depressed once to close the circuit, the motor 76 is energized, whereby the cam 77 rotates as shown in FIG. 11 to lower the drive shaft 67 against the resilience of the spring 74. As the drive shaft 67 moves down, the engagement between the cam groove 67a and the pin 69 causes the drive shaft 67 to rotate clockwise, as viewed in FIG. 12. The rotation of the drive shaft 67 brings forth an integral rotation of the rotating plate 70 through the engagement between the keyway 67b and the key 72, whereby the operating member 78 moves away from the limit switch S20 to close it. As a result, the motor 76 continues to rotate if the pushbutton switch $PS_O$ is released.

When the discharge port 64a of the tube 64 rotates and moves down to reach position 64aA above the vessel 62, shown in phantom line in FIG. 10, the operating member 78 engages the limit switch S10 to open it, whereby the motor 76 is stopped. The culture solution can then be injected into the vessel 62.

Subsequently when the pushbutton switch $PS_O$ is depressed again, the motor 76 and hence the cam 77 rotate to cause the drive shaft 67 to move upwardly under the influence of the cam 77 and the spring 74, now rotating in the counter-clockwise direction as viewed in FIG. 12. When the discharge port 64a reaches a position above the centrifuge tube 63, the motor is stopped by the action of the limit switch S20.

In the embodiment described above, the vertical movement of the drive shaft 67 has been controlled by the cam 77, but may be arranged to be achieved by the rotation of the rotating plate 70.

What is claimed is:

1. A liquid feeder for automatic culture apparatus comprising:
    a liquid storage container for storing a a liquid;
    a liquid suction and delivery pump for withdrawing said stored liquid from said container and for delivering said liquid through a liquid delivery port of said pump;
    a first tube interconnecting said pump with said container;
    a second tube extending through a wall of an incubator, which wall serves to isolate the environment in said incubator from the ambient environment, said second tube having a first end connected with said liquid delivery port of said pump and a second end directed towards a given position within said incubator; and
    a tube fitting extending through said wall and including an outer pipe hermetically secured to said wall and extending into said incubator, and also including an inner pipe which is hermetically and detachably secured to said outer pipe, said second end of said second tube extending through said inner pipe and surrounded by a silicone filler which seals and secures said second tube to said inner pipe.

2. A liquid feeder according to claim 1 in which said outer pipe has its outer periphery sealed and secured to said wall with silicone filler and has its lower end extending through a ceiling plate of said incubator and secured thereto around its outer periphery.

3. A liquid feeder according to claim 1 in which said silicone filler which seals and secures said outer pipe to said wall also prevents a leakage of the environment maintained within said incubator, the silicone filler filled inside said inner pipe, and an O-ring interposed between said outer and said inner pipe.

4. A liquid feeder according to claim 1 in which said second tube has a helical winding formed therein adjacent to said second end which is inserted into said incubator, said helical winding permitting said liquid being fed to be heated to the temperature of the environment maintained with the incubator.

5. A liquid feeder according to claim 1, wherein said liquid is a buffer solution.

6. A liquid feeder according to claim 1, wherein said liquid is an enzyme solution.

7. A liquid feeder according to claim 1, wherein said liquid is a culture solution.

8. A liquid feeder according to claims 7, 5 or 6 wherein said automatic culture apparatus further includes means for refrigerating said stored liquid.

* * * * *